United States Patent [19]

Cacheris et al.

[11] Patent Number: 5,614,170

[45] Date of Patent: *Mar. 25, 1997

[54] PARAMAGNETIC COMPLEXES OF N-ALKYL-N-HYDROXYLAMIDES OF ORGANIC ACIDS AND EMULSIONS CONTAINING SAME FOR MAGNETIC RESONANCE IMAGING (MRI)

[75] Inventors: William P. Cacheris, Florissant; Thomas J. Richard, Des Peres; Raymond C. Grabiak, Maryland Heights; Albert C. Lee, Chesterfield, all of Mo.

[73] Assignee: HemaGen/PFC, St. Louis, Mo.

[*] Notice: The portion of the term of this patent subsequent to Jun. 2, 2014, has been disclaimed.

[21] Appl. No.: 346,885

[22] Filed: Nov. 30, 1994

[51] Int. Cl.⁶ ............................................... A61B 5/055
[52] U.S. Cl. ........................ 424/9.365; 514/492; 514/502; 514/836
[58] Field of Search ............................ 424/9.365; 514/492, 514/502, 836; 556/50, 55, 63, 77, 105, 116, 134, 148; 534/16; 436/173; 128/653.4, 654

[56] References Cited

U.S. PATENT DOCUMENTS

| | | | |
|---|---|---|---|
| 3,962,439 | 6/1976 | Yokoyama et al. | 424/248 |
| 3,993,581 | 11/1976 | Yokoyama et al. | 252/312 |
| 4,110,474 | 8/1978 | Lagow et al. | 424/350 |
| 4,186,253 | 1/1980 | Yokoyama et al. | 435/240 |
| 4,187,252 | 2/1980 | Lagow et al. | 260/653 |
| 4,252,827 | 2/1981 | Yokoyama et al. | 424/366 |
| 4,423,077 | 12/1983 | Sloviter | 424/325 |
| 4,443,480 | 4/1984 | Clark, Jr. | 424/352 |
| 4,534,978 | 8/1985 | Yokoyama et al. | 514/429 |
| 4,542,147 | 12/1985 | Yokoyama et al. | 514/411 |
| 4,647,447 | 3/1987 | Gries et al. | 424/9 |
| 4,686,024 | 8/1987 | Scherer, Jr. et al. | 204/157 |
| 4,859,451 | 8/1989 | Quay et al. | 424/9 |
| 4,957,939 | 12/1990 | Gries et al. | 514/492 |
| 4,963,344 | 10/1990 | Gries et al. | 424/9 |
| 5,021,236 | 6/1991 | Gries et al. | 424/9 |
| 5,064,636 | 11/1991 | Li et al. | 424/9 |
| 5,120,527 | 6/1992 | Li et al. | 424/9 |
| 5,154,914 | 10/1992 | Elgavish et al. | 424/9.365 |
| 5,217,706 | 6/1993 | Rajagopalan et al. | 424/9.361 |
| 5,312,617 | 3/1994 | Unger et al. | 424/9.365 |
| 5,316,756 | 5/1994 | Gries et al. | 424/9.365 |
| 5,399,340 | 3/1995 | Radüchel | 424/9 |

FOREIGN PATENT DOCUMENTS

| | | |
|---|---|---|
| 0080716 | 6/1983 | European Pat. Off. . |
| 0158996 | 10/1985 | European Pat. Off. . |
| WO92/21017 | 11/1992 | WIPO . |

*Primary Examiner*—Gary E. Hollinden
*Attorney, Agent, or Firm*—Wood, Herron & Evans, P.L.L.

[57] ABSTRACT

Emulsions of paramagnetic contrast agents, and processes of making and using them are disclosed. The emulsions contain water, a dispersed oil phase and a complex of a paramagnetic metal ion and an organic acid chelator, for example DTPA (diethylenetriaminepentaacetic acid), having a $C_{10}$–$C_{30}$ saturated aliphatic group and an hydroxyl group bonded to the nitrogen atom. The emulsions are very stable and therapeutically acceptable for intravenous administration to enhance MRI imaging.

40 Claims, 2 Drawing Sheets

FINE

POOR

FIG. 1

PARAMAGNETIC COMPLEXES OF N-ALKYL-N-HYDROXYLAMIDES OF ORGANIC ACIDS AND EMULSIONS CONTAINING SAME FOR MAGNETIC RESONANCE IMAGING (MRI)

TECHNICAL FIELD OF THE INVENTION

This invention relates to paramagnetic complexes, emulsions containing same, and processes of making and using them. More particularly, this invention relates to novel emulsions that contain water, a dispersed oil phase and a complex of a paramagnetic metal ion and an organic acid chelator, for example DTPA (diethylenetriaminepentaacetic acid), having a $C_{10}$–$C_{30}$ saturated aliphatic group and an hydroxyl group bonded to a nitrogen atom. The emulsions are very stable and are therapeutically acceptable for intravenous administration to enhance MRI imaging.

BACKGROUND OF THE INVENTION

Magnetic resonance imaging (MRI) has been developed in recent years and, for improved imaging, paramagnetic contrast agents have been given to patients prior to imaging. A number of patents disclose paramagnetic MRI contrast agents including, for example, U.S. Pat. Nos. 4,647,447; 4,859,451; 4,957,939; 4,963,344; 5,021,236; 5,064,636 and 5,120,527; and PCT application WO 92/21017. These patents are considered to be illustrative of prior references in the field and are not intended to be the most pertinent references.

Paramagnetic agents of the type disclosed in the above patents have been administered to the patient in the form of aqueous solutions. In addition, paramagnetic oil emulsions have been provided for MRI imaging in the gastro-intestinal tract as disclosed in U.S. Pat. Nos. 5,064,636 and 5,120,527. There has been a continuing effort to develop complexes of paramagnetic metal ions as MRI contrast agents that function effectively as organ imaging agents as well as blood pool agents, or for other uses, such as agents for imaging the bone marrow, spleen, liver, or lymph nodes. Liposomes have also been studied as MRI contrast agents, and, more recently, as disclosed in PCT application WO 92/21017, lipo soluble contrast agents may be administered in the form of lipid emulsions. The contrast agents of the PCT application are useful in the imaging of the liver, blood pool and reticuloendothelial system (RES).

Notwithstanding the prior efforts in the field, there is a continuing need for improved MRI contrast agents. In particular, MRI contrast agents are needed which function effectively as organ imaging agents as well as blood pool agents, and for general imaging of the reticuloendothelial system. Stable and versatile MRI contrast agents are needed, especially for intravenous use.

SUMMARY OF THE INVENTION

This invention is directed to paramagnetic complexes for MRI and emulsions containing same. A physiologically acceptable emulsion for enhancement of MRI imaging comprises water, a dispersed oil phase and a complex of a paramagnetic metal ion and an organic chelator having the formula

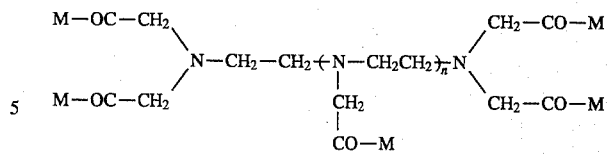

wherein from 2 to 5M groups are hydroxyl, n=0 to 2, and any remaining M group is $NR_1R_2$, each $R_1$ is a $C_{10}$–$C_{30}$ saturated aliphatic group and $R_2$ is hydroxyl. It has been discovered that very fine and stable emulsions may be made using such chelate complexes. These emulsions remain stable after heat stabilization. Moreover, these emulsions may be used intravenously and provide excellent MRI images.

The metal ion is a lanthanide element of atomic numbers 58–70 or a transition metal of atomic numbers 21–29, 42 or 44, most preferably selected from a group consisting of Gd(III), Mn(II), iron and dysprosium. The organic chelator is preferably an acid selected from the group consisting of ethylenediaminetetraacetic acid and diethylenetriaminepentaacetic acid. Mono- or bis- (N-alkyl-N-hydroxylamides) having a saturated $C_{14}$–$C_{22}$ group are physiologically preferred. It has been established that the unsaturated group may have one, two, or three double bond(s) at a number of different locations in the group, and very fine, stable emulsions are still achieved.

The MRI emulsions for intravenous administration have an average particle size less than about 1 micron, preferably on the order of about 0.2 to about 0.4 micron. In other embodiments, the emulsions comprise water, a dispersed oil phase selected from the group consisting of an oil and a fluorochemical, and mixtures thereof, a surfactant, and a dispersed complex of a paramagnetic metal ion and an organic chelator. The emulsified particles of an oil and/or a fluorochemical ("PFC") in water are hereinafter sometimes referred to as the "dispersed oil phase". The paramagnetic agent may be effectively suspended or dispersed in the stabilized emulsion for delivery to an animal or human subject.

In contrast to prior MRI agents and compositions, the MRI emulsions of this invention are very stable and exhibit excellent storage stability at room temperature or other ambient conditions. Furthermore, the inventive emulsions produce excellent MRI images of organs, blood pool and the RES.

This invention also includes methods of making emulsions containing paramagnetic agents. Other objectives of this invention and advantages will become apparent from the following detailed description.

DETAILED DESCRIPTION OF THE INVENTION

The MRI emulsions of this invention comprise an oil and/or a fluorochemical (PFC) emulsified in water and contain a paramagnetic metal chelate complex. In certain cases, the chelate complex may act as a surfactant and, thus, additional cosurfactant may not be needed. In most cases, a surfactant is added. In general, the oil and/or PFC may be contained in amounts from about 0.5 to 50% by weight. More specifically, for instance, in medical applications for intravenous (IV) MRI contrast agent delivery, the preferred amounts of PFC and/or oil with surfactant are minimum amounts to effectively disperse the agent in a stable emulsion. For oral, rectal, or other delivery, far greater amounts may be desirable. For IV use, about 25 w/v % is a practical limit for the oil, or about 55 v/v % for the PFC, because of viscosity limitations for an intravenous product. Preferred ranges are about 5 to 20 w/v % for the oil and about 5 to about 50 v/v % for the PFC. Emulsions exhibit high viscosity (or a gel-like consistency) at higher oil or PFC levels. The surfactant may be contained in amounts from about 0.5 to about 10% by weight, usually about 1–5% by weight of the emulsion. Generally, the MRI agent may be dispersed in varying amounts up to about 30% by weight, depending upon dose, efficacy and safety requirements. Thus, an IV emulsion may preferably contain an amount of MRI agent up to about 10% by weight. For instance, in oral or rectal administration, an MRI imaging agent such as a gadolinium salt of a bis(N-alkyl-N-hydroxylamide) of diethylenetriaminepentaacetic acid may be used as high as about 50% or more. If desired, the emulsions may be diluted with isotonic saline, or other agents, to produce lower concentrations. These components are identified with greater particularity as follows.

A. Paramagnetic Metal Chelate Complex

In a broad form, this invention is directed to a physiologically acceptable emulsion for enhancement of MRI imaging comprising water, a dispersed oil phase and a complex of a paramagnetic metal ion and an organic chelator having the formula

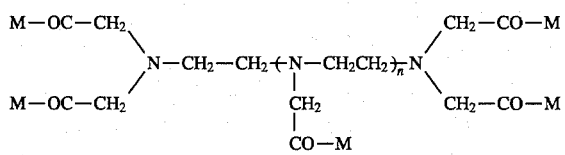

wherein from 2 to 5M groups are hydroxyl, n=0 to 2, and any remaining M group is $NR_1R_2$, each $R_1$ is a $C_{10}$–$C_{30}$ saturated aliphatic group and $R_2$ is hydroxyl. It has been discovered that very fine and stable emulsions may be made using such chelate complexes. Moreover, these emulsions may be used intravenously and provide excellent MRI images.

The metal ion is a lanthanide element of atomic numbers 58–70 or a transition metal of atomic numbers 21–29, 42 or 44, most preferably selected from a group consisting of Gd(III), Mn(II), iron and dysprosium. The organic chelator is preferably an acid selected from the group consisting of ethylenediaminetetraacetic acid and diethylenetriaminepentaacetic acid. Monohydroxylamides or bishydroxylamides of an organic acid selected from a group consisting of diethylenetriaminepentaacetic acid and ethylenediaminetetraacetic acid are used wherein each $R_1$ is a $C_{14}$–$C_{22}$ group selected from the group of stearyl, tetradecyl and hexadecyl.

Specific examples of chelate complexes include gadolinium diethylenetriaminepentaacetic acid bis(N-stearyl-N-hydroxylamide), gadolinium diethylenetriaminepentaacetic acid bis(N-tetradecyl-N-hydroxylamide), and gadolinium diethylenetriaminepentaacetic acid bis(N-hexadecyl-N-hydroxylamide).

B. Oil

The term "oil" is used herein in a general sense to identify a large class of physiologically acceptable substances whether of mineral, vegetable, animal, essential or synthetic origin. Thus, the term "oil" is used herein as applied to a wide range of substances that are quite different in chemical nature. In the classification of oils by type or function, for example mineral oil is derived from petroleum and includes aliphatic or wax-based hydrocarbons, aromatic hydrocarbons or mixed aliphatic and aromatic based hydrocarbons. Also included in the mineral classification are petroleum-derived oils such as refined paraffin oil, and the like. In the vegetable classification, oils are chiefly derived from seeds or nuts and include drying oils such as linseed and tung oil; semidrying such as safflower and soy bean oils; nondrying such as castor, cottonseed and coconut oils and edible soap stocks such as palm and coconut oils. In the animal classification, oils usually occur as fats in tallow, lard and stearic acid sources. The liquid animal types include fish oils, oleic acid, sperm oil, etc. and they usually have a high fatty acid content. Included are some vegetable oils, such as olive, cottonseed, corn and peanut, as well as some special fish oils such as cod-liver, haliver, shark liver, and so forth which are used largely as medicines for their high vitamin content. A liquid fatty oil such as a mono-, di-, or triglyceride, or a mixture thereof, is the preferred oil. Medium chain triglycerides also serve as useful oils according to this invention.

C. Fluorochemical

In this description, "fluorochemical" or "PFC" is used to describe either a highly fluorinated organic compound of perfluorocarbon or fluorinated chemical. Further, these terms are used interchangeably. The term "perfluorocarbon" includes a "cyclic" or "acyclic" compound of carbon. Substituted derivatives thereof are also included where fluorocarbons have other elements within their structures such as oxygen, hydrogen, nitrogen chlorine and bromine, etc. It should also be noted that the term "perfluorocarbon" is meant to include partially or substantially fluorinated compounds. This is permissible providing that the lack of complete replacement of all hydrogens does not affect the essential non-toxic characteristics of the preferred medical fluorocarbons of this invention. Among the perfluorocarbon compounds which may be employed are perfluorotributylamine (FC47), perfluorodecalin (PP5), perfluoromethyldecalin (PP9), perfluorooctylbromide, perfluorotetrahydrofuran (FC80), perfluoroether (PID) $[(CF_3)_2CFOCF_2(CF_2)_2CF_2OCF(CF_3)_2]$ perfluoroether (PIID) $[(CF_3)_2CFOCF_2(CF_2)_6CF_2OCF(CF_3)_2]$,

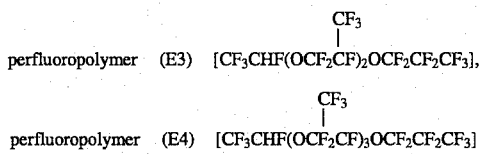

perfluoroetherpolymer (Fomblin Y/01), perfluorododecane, perfluorobicyclo[4.3.0.]nonane, perfluorotritrimethylblcyclohexane, perfluorotripropylamine, perfluoroisopropyl cyclohexane, perfluoroendotetrahydrodicyclopentadiene, perfluoroadamantane, perfluoroexotetrahydrodicyclopentadiene, perfluorbicyclo[5.3.0.]decane, perfluorotetramethylcyclohexane, perfluoro-1-methyl-4-isopropylcyclohexane, perfluoro-n-butylcyclohexane, perfluorodimethylbicyclo [3.3.1.]nonane, perfluoro-1-methyl adamantane, perfluoro-1-methyl-4-t butylcyclohexane, perfluorodecahydroacenapthane, perfluorotrimethylbicyclo [3.3.1.]nonane, perfluoro-1-methyl adamantane, perfluoro-1-methyl-4-t butylcyclohexane, perfluorodecahydroacenaphthene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1-3dimethyladamantane, perfluoro-n-octylcyclohexane, perfluoro-7-methyl bicyclo[4.3.0.]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4, 5-dihydro-4-octene, perfluorodichlorooctane and perfluorobischlorobutyl ether. Chlorinated perfluorocarbons, such as chloroadamantane and chloromethyladamantane as described in U.S. Pat. No. 4,686,024 may be used. Such compounds are described, for example in U.S. Pat. Nos. 3,962,439; 3,993,581; 4,110,474; 4,186,253; 4,187,252; 4,252,827; 4,423,077; 4,443,480; 4,534,978 and 4,542,147, European Patent Application Nos. 80716 and 158,996, British Patent specification 1,549,018 and German Offen. 2,650,586. Of course, it should be understood that mixtures of any of these highly fluorinated organic compounds may also be used in the emulsions and processes of this invention.

D. Surfactant

Surfactants are usually needed to form stable emulsions indicated above where the MRI agent has insufficient surfactant activity. Any suitable surfactant may be employed alone or in combination with other surfactants. For example, egg yolk phospholipids or Pluronics emulsifying agents may be used. Pluronics agents are block polymer polyols sold by Wyandotte, e.g., Pluronics F68, having a molecular weight of about 8,000, may be employed. Ethoxylates of cholesterol, diacyl glycerol and dialkyl ether glycerol are useful surfactants. Also, using backbones of cholesterol, diacyl glycerol or dialkyl ether glycerol, block copolymers are made by adding ethylene oxide, propylene oxide and ethylene oxide, in that order, in varying amounts to produce surfactants. In some applications for nonintravenous use, anionic or cationic surfactants may be used. The emulsions of this invention may contain alkylphosphoryl choline or alkylglycerophosphoryl choline surfactants described in Kaufman and Richard, U.S. Ser. No. 791,420, filed Nov. 13, 1991. Specific examples of these surfactants are 1,2-dioctylglycero-3-phosphoryl choline, 1,2-ditetradecylglycero-3-phosphoryl choline, 1,2-dihexadecylglycero-3-phosphoryl choline, 1,2-di-octadecylglycero-3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1-2-dioctadecylglycero-3-phosphoryl choline, 1-octadecyl-2-hexadecylglycero-3-phosphoryl choline, 1-tetradecyl-2-hexadecylglycero-3-phosphoryl choline, 2,2-ditetradecyl-1-phosphoryl choline ethane and 1-hexadecyl-tetradecylglycero-3-phosphoryl choline. The 1,3-dialkyl glycerophosphoryl choline surfactants as described in Kaufman and Richard, U.S. Ser. No. 228,224, filed Apr. 15, 1994 may also be used and the disclosure thereof is incorporated herein by references. Mixtures of these novel surfactants with other known surfactants may also be employed. Anionic surfactants include alkyl or aryl sulfates, sulfonates, carboxylates or phosphates. Cationic surfactants include such as mono-, di-, tri- and tetraalkyl or aryl ammonium salts. Non-ionic surfactants include alkyl or aryl compounds, whose hydrophilic part consists of polyoxyethylene chains, sugar molecules, polyalcohol derivatives or other hydrophilic groups. Zwitter-ionic surfactants may have a combination of the above anionic or cationic groups, and whose hydrophobic part consists of any other polymer, such as polyisobutylene or polypropylene oxides.

E. Emulsion Characteristics

The emulsions of this invention are made by dispersing the above ingredients in water and homogenizing them. The oil and/or PFC are dispersed in the water and enhance the dispersion of the paramagnetic metal chelate complex. The surfactant enhances the dispersion by stabilization of the liquid phases. While dispersions may be generally referred to herein as emulsions, it should be understood that they may be considered solutions, micellar solutions, microemulsions, vesicular suspensions, or mixtures of all of these physical states. The PFC may be dispersed in the oil and the oil-PFC phase emulsified in the water. However, other possible interfaces and phases are within the scope of the invention. Accordingly, the term "emulsion" as used herein covers all these states and the surfactant is employed to enhance stable mixtures of these physical states of the fluorochemical, oil, paramagnetic metal chelate complex and water phases. For example, a fluorochemical and oil may be emulsified in water, as described in the Clark and Shaw European Pat. Appln. 87300454.3 and this application is incorporated herein by reference to describe suitable PFC/oil emulsions as MRI delivery agents.

The MRI emulsions of this invention are very fine, stable emulsions. The criterion for a "fine" emulsion is no visible solid matter microscopically (300–400×) and less than 10 volume % of particles above about 0.8 μm ("CV"). The "poor" emulsions of comparative prior art, for example, have a large amount of huge (>5 μm) solids visible under the microscope, as well as greater than 10 volume % of particles above about 0.8 μm ("CV"). Reference is made to FIG. 1 of the drawings which documents photographically the microscopic appearance of fine and poor emulsions at 300–400×. In FIG. 1, the fine emulsion contains 2% lecithin, 10% safflower oil and 5% GdDTPA-bis(N-stearyl-N-hydroxylamide) of this invention (Table 9). The poor emulsion has the same components except that it contains GdDTPA-bis-(stearylamide) of Table 6 for comparison. Thus, these two complexes make markedly different quality emulsions although the complexes differ only in the hydroxyl group.

BRIEF DESCRIPTION OF THE DRAWINGS

Figure 1:
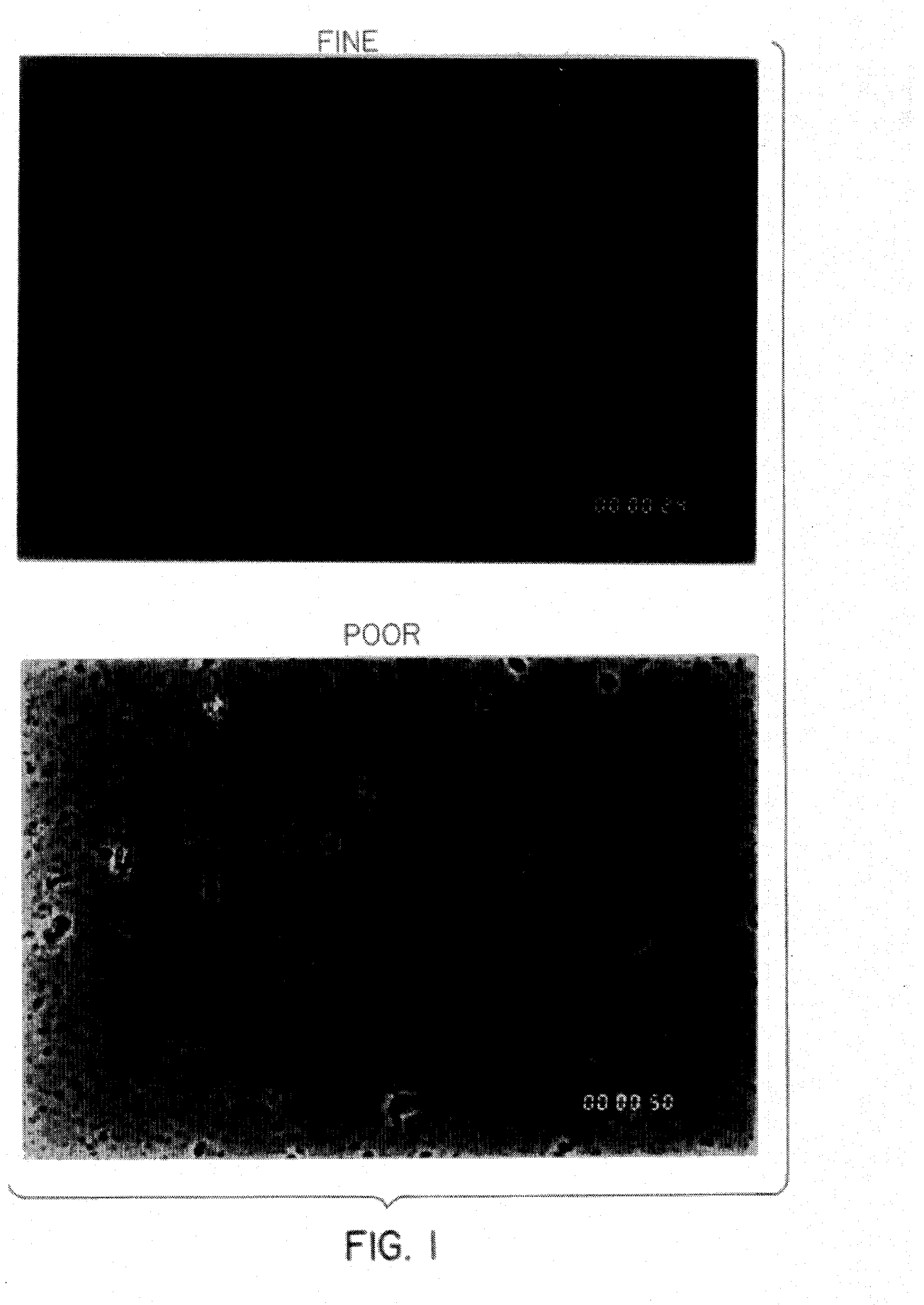

FIG. 1 depicts photographs of fine and poor emulsions at 300–400×.

Figure 2:
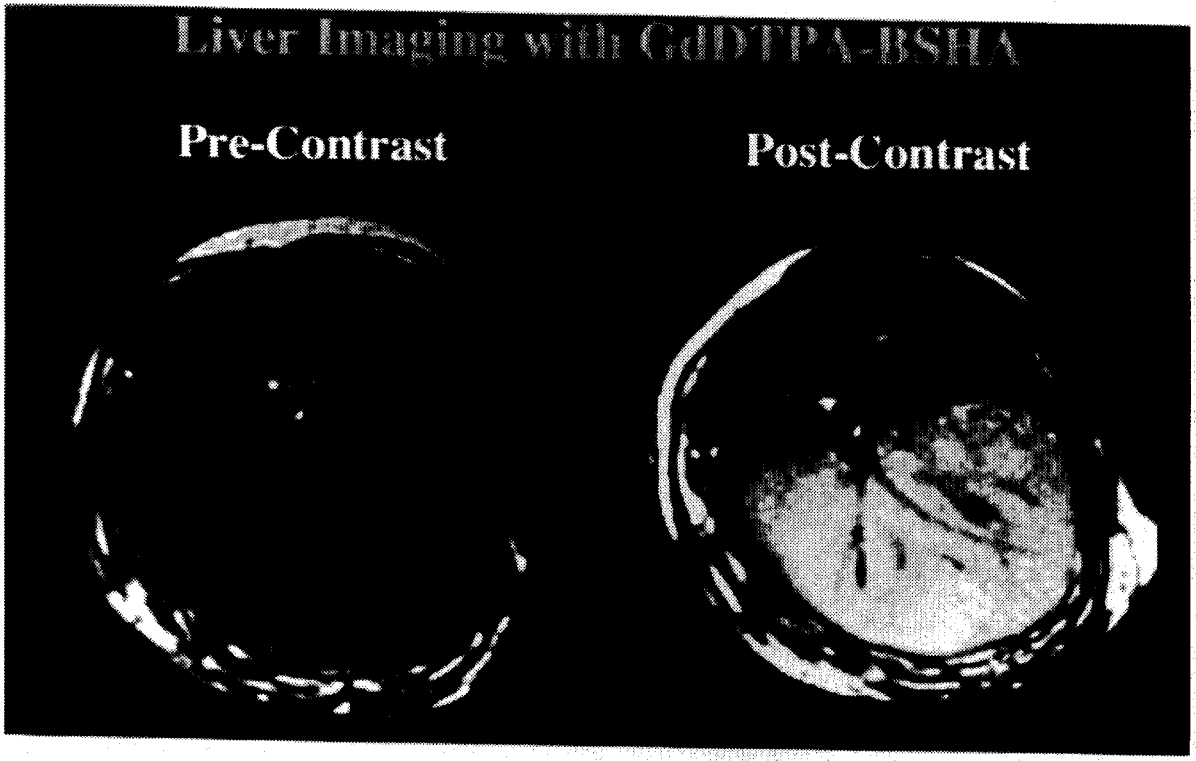
FIG. 2 depicts pre-contrast and post-contrast photographic MRI images of a liver.

The following non-limiting examples illustrate the various embodiments of this invention.

General Procedure for DTPA Bis(N-alkyl-N-hydroxylamides)

Under a static nitrogen atmosphere or a CaSO4 drying tube, a mechanically stirred mixture of diethylenetriaminepentaacetic (DTPA) dianhydride (1 mole) and anhydrous pyridine (2–24.7 mole; preferably 3.3 mole) in chloroform (0–3 L/mole of DTPA dianhydride; preferably 1 L/mole) was treated dropwise with a solution of the appropriate hydroxylamine (2 mole) in chloroform (0–2.5 L/mole of hydroxylamine; preferably 0.25 L/mole). In some cases, a mild exotherm was apparent. The resulting mixture was then heated at reflux (65° C. w/o chloroform solvent) for 17–22 hours.

Workup Procedure A: After cooling to ambient temperature, the resulting reaction mixture was diluted with acetone (4–5 L/L of CHCl3) and cooled to 0° C. The resulting solid was filtered and washed with acetone. In some cases, the resulting solid was purified further by recrystallization from appropriate solvent to give the corresponding DTPA Bis(N-alkyl-N-hydroxylamide) (See Table 1 for more details). These compounds were characterized by elemental analyses (see Table 2), infrared spectroscopy, proton and carbon nuclear magnetic resonance spectroscopy. High performance liquid chromatography was also used to assess purity on some derivatives.

Workup Procedure B: If no precipitate was obtained with acetone dilution on a small aliquot, the resulting reaction mixture was washed with 5% HCl to remove the pyridine and then with saturated brine solution. After drying over $MgSO_4$, concentration in vacuo yielded the crude DTPA Bis(N-alkyl-N-hydroxylamide) as a beige, glassy material (See Table 1 for more details). In some cases, column chromatography on silica gel with chloroform and methanol mixtures was used to remove trace impurities. These compounds were characterized further by elemental analyses (see Table 3), infrared spectroscopy, proton and carbon nuclear magnetic resonance spectroscopy. High performance liquid chromatography was also used to assess purity.

The above procedures were used to make various DTPA Bis(N-alkyl-N-hydroxylamide) ligands. The following plex/L of solvent) was heated at reflux with stirring for 18–25 hrs. After cooling to ambient temperature, the solution was filtered through Celite to remove trace $Gd_2O_3$. The filtrate was concentrated in vacuo to yield an off-white solid or glass. The resulting solid was recrystallized from appropriate solvent or slurried in hot acetone as shown in Table 2 unless noted otherwise. In some cases, the resulting solid was dried in a vacuum oven at 50°–65° C. and 29" Hg vacuum overnight. Successful complexation was evident by the dissolution of $Gd_2O_3$ into the organic solvent mix, thin layer chromatography (TLC) relative to the free ligand and infrared spectroscopy. Alternatively, $GdCl_3 \cdot 6H_2O$ could be used to form the complex. Completion of the reaction could be monitored by TLC. Upon completion of the reaction, aq. NaOH was used to neutralize the reaction mixture and precipitated NaCl was removed by filtration through Celite. In general, high performance liquid chromatography (HPLC) of the isolated products were greater than 90% one component. In the case of the unsymmetrically N,N-disubstituted DTPA hydroxylamides, four major peaks were evident by TLC and HPLC analyses suggesting isomers due to the two achiral nitrogen atoms in the complexed ligand and restricted rotation around amide bonds. Elemental analyses of these complexes were also performed and reported in Table 3.

TABLE 2

| | Gd.DTPA Bis(N-alkyl-N-hydroxylamide) Complexes | | | | |
|---|---|---|---|---|---|
| Compound | $R_1$ | $R_2$ | Recryst Solvent | Yield | mp (°C.) |
| GdDTPA-BSHA | Stearyl | OH | $Et_2O/CHCl_3$ | 73% | 98–100 |
| GdDTPA-BHDHA | Hexadecyl | OH | Chromatography | 99% | 255 (dec) |
| GdDTPA-BTDHA | Tetradecyl | OH | Chromatography | 47% | 255 (dec) |

TABLE 3

| | Elemental Analyses of GD.DTPA Bis(N-alkyl-N-hydroxylamide) Complexes | | | | | | | |
|---|---|---|---|---|---|---|---|---|
| | | | | Weight Per Cent Found (Calcd) | | | | |
| Compound | $R_1$ | $R_2$ | Molecular Formula | C | H | N | Gd | Water |
| GdDTPA-BSHA | Stearyl | OH | $C_{50}H_{94}N_5O_{10}Gd \cdot 2H_2O$ | 52.54 (53.54) | 8.79 (9.08) | 5.89 (6.24) | 14.28 (14.02) | 3.59 (3.21) |
| GdDTPA-BHDHA | Hexadecyl | OH | $C_{56}H_{102}N_5O_8Gd \cdot H_2O$ | 53.17 (52.90) | 8.73 (8.49) | 6.45 (6.71) | 17.01 (15.06) | 2.06 (1.72) |
| GdDTPA-BTDHA | Tetradecyl | OH | $C_{46}H_{84}N_5O_8Gd \cdot 1.5 H_2O \cdot 1.5 HCl$ | 47.89 (47.95) | 7.67 (7.90) | 6.43 (6.66) | 17.63 (14.95) | 2.38 (2.57) |

Table 1 provides a variety of N $R_1$ $R_2$ groups under the above general formula in accordance with Workup A or B.

TABLE 1

| DTPA Bis(N-alkyl-N-hydroxylamide) Ligands | | |
|---|---|---|
| $R_1$ | $R_2$ | Workup Procedure |
| Stearyl ($C_{18}H_{37}$) | OH | Solvent Stripped |
| Hexadecyl ($C_{16}H_{33}$) | OH | Solvent Stripped |
| Tetradecyl ($C_{14}H_{29}$) | OH | Solvent Stripped |

General Procedure for Gadolinium Complexes with DTPA Bis(N-alkyl-N-hydroxylamide) Ligands A stoichiometric equivalent of gadolinium oxide and the corresponding DTPA Bis(N-alkyl-N-hydroxylamide) in 75:22:3 (V/V/V) $CHCl_3:CH_3OH:H_2O$ (≈0.1 mole of com- The MRI emulsions of this invention that have been made in accordance with the above detailed description were characterized into various categories of emulsions for comparison with other paramagnetic metal ion chelate complexes outside the scope of this invention. According to this invention, the paramagnetic metal chelate complexes that make fine emulsions have been categorized as those in accordance with the above general formula where $R_1$ is a long carbon chain ($C_{10}$–$C_{30}$) on the nitrogen that is saturated and $R_2$ is hydroxyl. The categories of emulsions and complexes of this invention that make fine emulsions are compared to other emulsions and complexes that make poor emulsions as reported in Table 5. A key to the ligands of the complexes of this invention and other complexes is provided in Table 4.

TABLE 4

Key to Ligands

BSA = bis(stearylamide)
BHESA = bis(N-hydroxyethyl-N-stearylamide)
BODP = bis(N-octadecyl-N-propanediolamide)
BDDA = bis(dodecylamide)
BTDA = bis(tetradecylamide)
BSHA = bis(N-stearyl-N-hydroxylamide)
BHDHA = bis(N-hexadecyl-N-hydroxylamide)
BBuOA = bis(N-butyl-N-oleylamide)
BPOA = bis(N-propyl-N-oleylamide)

BMSA = bis(N-methyl-N-stearylamide)
BHDPA = bis(N-hexadecylphenylamide)
BHDA = bis(N-hexadecylamide)
BDOA = bis((N,N-dioctyl)amide)
BTDHA = bis(tetradecyl-N-hydroxylamide)
BDOlA = bis(N-benzyl-N-oleylamide)
BBOA = bis(N-benzyl-N-oleylamide)

TABLE 5

Categories of Emulsions and Complexes

| $R_1$ | $R_2$ | Category # |
|---|---|---|
| Poor (comparative) | | |
| $C_{\geq 10}$ - Saturated | H | 1 |
| $C_{\geq 10}$ - Saturated | $C_{\geq 1}$ - Saturated | 2 |
| $C_{\geq 10}$ - Unsaturated | $C_{>2}$ Sat./Unsat. | 3 |
| Fine (invention) | | |
| $C_{\geq 10}$ - Saturated | OH | 4 |

As may be determined from the above Table 5, the emulsions and chelate complexes of category 4 are representative of those MRI chelate complexes that make fine emulsions in accord with this invention. Those emulsions and chelate complexes of categories 1–3 make poor emulsions. The tabular summaries for each of the above categories 1–4 are reported in the following Tables 6–8.

TABLE 6

Comparative Category #1 (single saturated chain)

| Active Component | % lec./% oil | Quality | $R_1$ | $R_2$ | Visc | PSD | CM | CV |
|---|---|---|---|---|---|---|---|---|
| 5% GdDTPA-BSA | 2/10 | Solids | $C_{18}H_{37}$ | H | 35.70 | 194 | 6.54 | 48.4 |
| 5% GdDTPA-BSA | 2/5 | Solids | $C_{18}H_{37}$ | H | * | 212 | 8.28 | 98.8 |
| 5% GdDTPA-BSA | 2/20 | Solids | $C_{18}H_{37}$ | H | * | 191 | 7.11 | 72.8 |
| 5% GdDTPA-BSA | 4/10 | Solids | $C_{18}H_{37}$ | H | 9.44 | 194 | 7.73 | 82.4 |
| 5% GdDTPA-BSA | 4/5 | Solids | $C_{18}H_{37}$ | H | 9.77 | 188 | 7.83 | 86.6 |
| 5% GdDTPA-BSA | 4/20 | Solids | $C_{18}H_{37}$ | H | 9.52 | 269 | 5.85 | 32.9 |
| 5% GdDTPA-BDDA | 2/10 | Solids | $C_{12}H_{25}$ | H | 1.8 | 210 | 2.34 | 19.8 |
| 5% GdDTPA-BHDA | 2/10 | Solids | $C_{16}H_{33}$ | H | 2.59 | 184 | 3.55 | 39.8 |
| 5% GdDTPA-BTDA | 2/10 | Solids | $C_{14}H_{29}$ | H | 1.55 | 196 | 2.73 | 18.24 |
| 5% GdDTPA-BHDPA | 2/10 | Solids | $C_{22}H_{37}$ | H | 2.82 | 195 | 6.63 | 100 |

FOOTNOTE FOR TABLES 6–9
Quality = as viewed at 1200X
Visc. = viscosity in centipose (cP)
CM = mean particle size above 0.78 μm
PSD = submicron mean particle size (nm)
CV = volume percent of particles above 0.78 μm

TABLE 7

Comparative Category #2 (two saturated chains)

| Active Component | % lec./% oil | Quality | $R_1$ | $R_2$ | Visc | PSD | CM | CV |
|---|---|---|---|---|---|---|---|---|
| 5% GdDTPA-BMSA | 2/10 | Solids | $C_{18}H_{37}$ | $CH_3$ | 2.04 | 532 | 2.41 | 12.52 |
| 5% MnEDTA-BODP | 2/10 | Solids | $C_{18}H_{37}$ | $C_3H_7O_2$ | 2.87 | 187 | 4.139 | 35.40 |
| 5% GdDTPA-BDOA | 2/10 | Failed | $C_8H_{17}$ | $C_8H_{17}$ | | | | |

TABLE 8

Comparative Category #3 (one unsaturated chain, one long chain C > 2)

| Active Component | % lec./% oil | Quality | $R_1$ | $R_2$ | Visc | PSD | CM | CV |
|---|---|---|---|---|---|---|---|---|
| 5% GdDTPA-BDOlA | 2/10 | Failed | $C_{18}H_{35}$ | $C_{18}H_{35}$ | — | — | — | — |
| 5% GdDTPA-BBOA | 2/10 | Failed | $C_{18}H_{35}$ | $C_7H_7$ | — | — | — | — |
| 5% GdDTPA-BPOA | 2/10 | Solids | $C_{18}H_{35}$ | $C_3H_7$ | 24.4 | 569 | 7.11 | 43.1 |

TABLE 8-continued

Comparative Category #3 (one unsaturated chain, one long chain C > 2)

| Active Component | % lec./% oil | Quality | $R_1$ | $R_2$ | Visc | PSD | CM | CV |
|---|---|---|---|---|---|---|---|---|
| 5% GdDTPA-BBuOA | 2/10 | Solids | $C_{18}H_{35}$ | $C_4H_9$ | 2.17 | * | 9.12 | 54.4 |
| 5% GdDTPA-BHOA | 2/10 | Failed | $C_{18}H_{35}$ | $C_6H_{13}$ | — | — | — | — |

TABLE 9

Invention Category #4 (one —OH, and one saturated chain C ≧ 10)

| Active Component | % lec./% oil | Quality | $R_1$ | $R_2$ | Visc | PSD | CM | CV |
|---|---|---|---|---|---|---|---|---|
| 5% GdDTPA-BSHA | 2/10 | Excellent | $C_{18}H_{37}$ | OH | 1.64 | 192 | 1.06 | 1.00 |
| 5% GdDTPA-BHDHA | 2/10 | Very Good | $C_{16}H_{33}$ | OH | 1.94 | 185 | 1.64 | 1.36 |
| 5% GdDTPA-BTDHA | 2/10 | Excellent | $C_{14}H_{29}$ | OH | 2.30 | 171 | 1.29 | 0.20 |

With respect to Comparative Category #1 as represented by Table 6, it was found that where $R_1$ was a single saturated chain and $R_2$ was hydrogen as represented by GdDTPA-BSA, poor emulsions were made despite a variety of compositions containing a surfactant lecithin, oil and PFDCO. Furthermore, with respect to those emulsions indicated by an asterisk(*), they were too viscous to measure. With reference to Comparative Categories #2 and #3 in Tables 7 and 8, where $R_1$ and $R_2$ were two saturated chains or one unsaturated chain and one long chain C>2, the emulsions had huge solids or simply failed to emulsify. In Table 8, the asterisk (*) indicates that the emulsion cracked upon sterilization and the particle sizes were too large to be measured by sub-micron particle sizer.

In contrast, the invention is represented by Table 9 where Category No. 4 is shown. In other words, where $R_1$ was a $C_{10}$–$C_{30}$ saturated chain and $R_2$ was hydroxyl, excellent emulsions were obtained.

Furthermore, at the present time, the most preferred paramagnetic metal chelate complex is GdDTPA-BSHA which provides for an excellent emulsion with CVs above 0.8 micron about 1%.

The MRI utilities of the emulsion have been determined by using an emulsion containing 5% GdDTPA-BSHA to enhance the liver of a rabbit. FIG. 2 shows that nearly 100% enhancement occurs in the liver after intravenous administration of a 10 μmole of gadolinium per/kg dose. The enhancement effect on the liver persisted for at least one hour. The images were collected with a standard $T_1$-weighted spin-echo imaging sequence on a General Electric Signa whole body clinical scanner operating at 1.5 Tesla.

For comparison with the emulsions of this invention, Examples I and VII were reproduced from U.S. Pat. No. 5,120,527, mentioned in the above background of this invention. Although the emulsions made under this '527 patent according to these procedures do not have visible solids, they have very large particles on the order of 10 to about 30 microns and hence are unacceptable for IV use. With respect to the emulsion containing Geritol®, the composition contained 60 mL Geritol®, 150 mL melted ice cream, 250 mL milk and 100 mL corn oil; with other properties including viscosity of 6.05 cp, CM of 8.17 microns and CV of 83.1%. The Geritol® emulsion also cracked upon sterilization. The GdDTPA emulsion contained 0.5 mole (1.0 mL) of GdDTPA, 150 mL melted ice cream, 250 mL milk and 100 mL corn oil; with the other properties of the emulsion including a viscosity with 8.18 cp, CM of 16.3 microns and CV of 71.8%. In summary, the emulsions of the '527 patent are unacceptable for IV use and do not have the versatility of the emulsions of this invention. They also lack stability upon sterilization as evidenced by the above experiments.

In view of the above detailed description, other variations or modifications may be made without departing from the spirit and scope of this invention.

What is claimed is:

1. A complex of a paramagnetic metal ion and an organic chelator having the formula

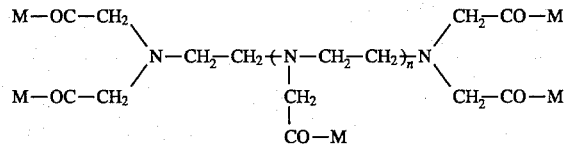

wherein from 2 to 5M groups are hydroxyl, n=0 to 2, and at least one remaining M group is $NR_1R_2$, each $R_1$ is a $C_{10}$–$C_{30}$ saturated aliphatic group and $R_2$ is hydroxyl.

2. The complex of claim 1 wherein said metal ion is a lanthanide element of atomic numbers 58–70 or a transition metal of atomic numbers 21–29, 42 or 44.

3. The complex of claim 1 wherein said metal ion is selected from a group consisting of Gd(III), Mn(II), iron and dysprosium.

4. The complex of claim 1 wherein said organic chelator is an acid selected from the group consisting of ethylenediaminetetraacetic acid and diethylenetriaminepentaacetic acid.

5. The complex of claim 1 Wherein each $R_1$ is $C_{14}$–$C_{22}$.

6. The complex of claim 1 wherein the organic chelator is a mono or bis(N-alkyl-N-hydroxylamide) where $R_1$ is selected from the group consisting of stearyl, tetradecyl and hexadecyl.

7. The complex of claim 1 wherein said complex is selected from the group of gadolinium diethylenetriaminepentaacetic acid bis(N-stearyl-N-hydroxylamide), gadolinium diethylenetriaminepentaacetic acid bis(N-tetradecyl-N-hydroxylamide), or gadolinium diethylenetriaminepentaacetic acid bis(N-hexadecyl-N-hydroxylamide).

8. A physiologically acceptable emulsion for enhancement of MRI imaging comprising water, a dispersed oil phase and a complex of a paramagnetic metal ion and an organic chelator having the formula

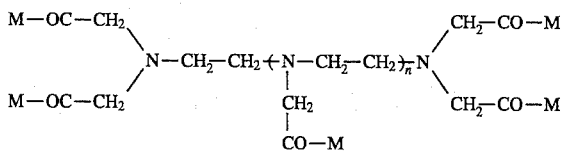

wherein from 2 to 5M groups are hydroxyl, n=0 to 2, and at least one remaining M group is $NR_1R_2$, each $R_1$ is a $C_{10}$–$C_{30}$ saturated aliphatic group and $R_2$ is hydroxyl.

9. The physiologically acceptable emulsion of claim 8 wherein said metal ion is a lanthanide element of atomic numbers 58–70 or a transition metal of atomic numbers 21–29, 42 or 44.

10. The physiologically acceptable emulsion of claim 8 wherein said metal ion is selected from a group consisting Gd(III), Mn(II), iron and dysprosium.

11. The physiologically acceptable emulsion of claim 8 wherein said organic chelator is an acid selected from the group consisting of ethylenediaminetetraacetic acid and diethylenetriaminepentaacetic acid.

12. The physiologically acceptable emulsion of claim 8 wherein each $R_1$ is $C_{14}$–$C_{22}$.

13. The physiologically acceptable emulsion of claim 8 wherein the organic chelator is a mono or bis(N-alkyl-N-hydroxylamide) where $R_1$ is selected from the group consisting of stearyl, tetradecyl and hexadecyl.

14. The physiologically acceptable emulsion of claim 8 wherein said complex is gadolinium diethylenetriaminepentaacetic acid bis(N-stearyl-N-hydroxylamide), gadolinium diethylenetriaminepentaacetic acid bis(N-tetradecyl-N-hydroxylamide), or gadolinium diethylenetriaminepentaacetic acid bis(N-hexadecyl-N-hydroxylamide).

15. The physiologically acceptable emulsion of claim 8 having an average particle size less than about 1 micron.

16. The emulsion of claim 8 that is stable after heat stabilization with less than 10 volume % of particles above about 0.8 micron.

17. The emulsion of claim 8 wherein the oil phase contains about 5 to about 25% w/v oil or about 5 to about 55% v/v fluorochemical.

18. The emulsion of claim 8 wherein the oil is selected from the group consisting of mono-, di- and triglycerides, and mixtures thereof.

19. The emulsion of claim 17 wherein a surfactant is present in an amount of about 0.5 to about 10% by weight of the emulsion.

20. A physiologically acceptable emulsion for enhancement of MRI imaging comprising water, a dispersed oil phase selected from the group consisting of an oil and fluorochemical, and mixtures thereof, a surfactant, and a complex of a paramagnetic metal ion and an organic chelator having the formula

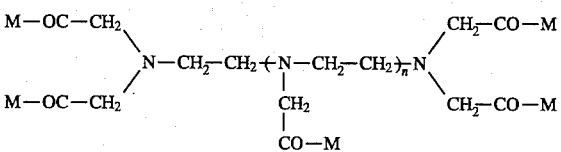

wherein from 2 to 5M groups are hydroxyl, n=0 to 2 and at least one remaining M group is $NR_1R_2$, each $R_1$ is a $C_{10}$–$C_{30}$ saturated aliphatic group and $R_2$ is hydroxyl.

21. The physiologically acceptable emulsion of claim 20 wherein said metal ion is a lanthanide element of atomic numbers 58–70 or a transition metal of atomic numbers 21–29, 42 or 44.

22. The physiologically acceptable emulsion of claim 20 wherein said metal ion is selected from a group consisting Gd(III), Mn(II), iron and dysprosium.

23. The physiologically acceptable emulsion of claim 20 wherein said organic chelator is an acid selected from the group consisting of ethylenediaminetetraacetic acid and diethylenetriaminepentaacetic acid.

24. The physiologically acceptable emulsion of claim 20 wherein each $R_1$ is $C_{14}$–$C_{22}$.

25. The physiologically acceptable emulsion of claim 20 wherein said complex is gadolinium diethylenetriaminepentaacetic acid bis(N-stearyl-N-hydroxylamide), gadolinium diethylenetriaminepentaacetic acid bis(N-tetradecyl-N-hydroxylamide), or gadolinium diethylenetriaminepentaacetic acid bis(N-hexadecyl-N-hydroxylamide).

26. The emulsion of claim 20 wherein the fluorochemical is selected from the group consisting of perfluorodecalin, perfluoromethyldecalin, perfluorodimethyladamantane, perfluorooctylbromide, perfluoro-4-methyloctahydroquinolidizine, perfluoro-N-methyl-decahydroquinoline, F-methyl-1-oxadecalin, perfluorobicyclo (5.3.0.) decane, perfluorooctahydroquinolidizine, perfluoro 5,6-dihydro-5-decene, perfluoro-4,5-dihydro-4-octene, perfluorodichlorooctane, perfluorobischlorobutyl ether, and chlorinated perfluorocarbons, and mixtures thereof.

27. The emulsion of claim 20 that is stable after heat sterilization with less than 10 volume % of particles above about 0.8 micron.

28. The emulsion of claim 20 wherein the oil phase contains about 5 to about 25% w/v oil or about 5 to about 55% v/v fluorochemical.

29. The emulsion of claim 20 wherein the oil is selected from the group consisting of mono-, di- and triglycerides, and mixtures thereof.

30. The emulsion of claim 20 having an average particle size less than about 1 micron.

31. The emulsion of claim 30 having an average particle size of about 0.2 to about 0.4 micron.

32. The emulsion of claim 28 wherein the surfactant is present in an amount from about 0.5 to about 10% by weight of the emulsion.

33. The method for MRI imaging of a subject comprising administering to such subject an image-modifying effective amount of the complex of claim 1.

34. The method for MRI imaging of a subject comprising administering to such subject an image-modifying effective amount of the complex of claim 3.

35. The method for MRI imaging of a subject comprising administering to such subject an image-modifying effective amount of the emulsion of claim 8.

36. The method for MRI imaging of a subject comprising intravenously administering to such subject an image-modifying effective amount of the emulsion of claim 20.

37. The method for MRI imaging of a subject comprising administering to such subject an image-modifying effective amount of the emulsion of claim 22.

38. The method for MRI imaging of a subject comprising administering to such subject an image-modifying effective amount of the emulsion of claim 24.

39. The method for MRI imaging of a subject comprising administering to such subject an image-modifying effective amount of the emulsion of claim 27.

40. The method for MRI imaging of a subject comprising intravenously administering to such subject an image-modifying effective amount of the emulsion of claim 28.

* * * * *